(12) United States Patent
Gong et al.

(10) Patent No.: US 10,758,160 B2
(45) Date of Patent: Sep. 1, 2020

(54) BODY PART MOTION ANALYSIS WITH WEARABLE SENSORS

(71) Applicant: Figur8, Inc., Boston, MA (US)

(72) Inventors: Nan-Wei Gong, Cambridge, MA (US); Jennifer Maria Brine, Somerville, MA (US); Marius Gailius, Cambridge, MA (US); Tiegeng Ren, Westford, MA (US); Donna Susan Scarborough, Hingham, MA (US)

(73) Assignee: Figur8, Inc., Boston, MA (US)

( * ) Notice: Subject to any disclaimer, the term of this patent is extended or adjusted under 35 U.S.C. 154(b) by 0 days.

(21) Appl. No.: 15/995,241

(22) Filed: Jun. 1, 2018

(65) Prior Publication Data
US 2018/0271409 A1    Sep. 27, 2018

Related U.S. Application Data

(63) Continuation-in-part of application No. 15/875,311, filed on Jan. 19, 2018.
(Continued)

(51) Int. Cl.
*A61B 5/11* (2006.01)
*G01B 7/16* (2006.01)
*A61B 5/00* (2006.01)

(52) U.S. Cl.
CPC ........... *A61B 5/1107* (2013.01); *A61B 5/1118* (2013.01); *A61B 5/1121* (2013.01);
(Continued)

(58) Field of Classification Search
CPC .... G01B 7/02; G01B 7/16; G01B 7/22; A61B 5/6804; A61B 5/746; A61B 5/1075;
(Continued)

(56) References Cited

U.S. PATENT DOCUMENTS 6,543,299 B2   4/2003 Taylor
7,173,437 B2   2/2007 Hervieux et al.
(Continued)

FOREIGN PATENT DOCUMENTS

JP        04-012201 A      1/1992
WO    WO2005067796 A1   7/2005

OTHER PUBLICATIONS

International Search Report dated Sep. 1, 2018 for PCT/US2018/035553.
(Continued)

*Primary Examiner* — Amy He
(74) *Attorney, Agent, or Firm* — Adams Intellex, PLC

(57) ABSTRACT

Disclosed embodiments describe techniques for body part motion analysis. A stretch sensor is attached to a body part. Tape can be applied to the body part, and the stretch sensor can be attached to the tape using connectors, hooks, snaps, or Velcro™. The stretch sensor changes electrical characteristics as it stretches. A sensor coupled to the stretch sensor collects changes in electrical characteristics based on motion of the body part. A communication unit provides information from the sensor to a receiving unit. Motion of the body part is shown on a display. The displayed body part can be an animation and can be displayed in the context of an overall body. The stretch sensor is used for measuring body part motion. An inertial measurement unit provides augmented motion information. The stretch sensor senses muscle activities such as muscle activation and deformation and provides movement angle, force and torque evaluation.

25 Claims, 13 Drawing Sheets

Related U.S. Application Data

(60) Provisional application No. 62/513,746, filed on Jun. 1, 2017, provisional application No. 62/448,525, filed on Jan. 20, 2017, provisional application No. 62/464,443, filed on Feb. 28, 2017.

(52) U.S. Cl.
CPC .............. *A61B 5/6831* (2013.01); *G01B 7/16* (2013.01); *G01B 7/22* (2013.01); *A61B 5/1126* (2013.01); *A61B 5/6802* (2013.01); *A61B 5/6824* (2013.01); *A61B 5/6828* (2013.01); *A61B 2562/0219* (2013.01); *A61B 2562/0261* (2013.01)

(58) Field of Classification Search
CPC ............ A61B 5/1072; A61B 2562/026; A61B 5/1107; A61B 5/1121; A61B 5/1118; A61B 5/6824; A61B 5/6802; A61B 5/6831; A61B 5/1126
USPC ........................................ 324/658, 671, 691
See application file for complete search history.

(56) References Cited

U.S. PATENT DOCUMENTS

| | | |
|---|---|---|
| 7,310,883 B1 | 12/2007 | Park |
| 7,817,095 B2 | 10/2010 | Lommen et al. |
| 8,161,826 B1 | 4/2012 | Taylor |
| 8,191,433 B2 | 6/2012 | Tao et al. |
| 8,327,721 B2 | 12/2012 | Bratkovski et al. |
| 8,668,653 B2 | 3/2014 | Nagata et al. |
| 8,818,478 B2 | 8/2014 | Scheffler et al. |
| 8,840,548 B2 | 9/2014 | Mazzarolo |
| 8,961,439 B2 | 2/2015 | Yang et al. |
| 9,423,311 B2 | 8/2016 | Moslehi |
| 9,855,484 B1* | 1/2018 | Matak ................... A63B 71/06 |
| 2003/0181832 A1 | 9/2003 | Carnahan et al. |
| 2004/0059242 A1 | 3/2004 | Masuo et al. |
| 2009/0094138 A1 | 4/2009 | Sweitzer et al. |
| 2009/0282671 A1 | 11/2009 | Tao et al. |
| 2009/0292193 A1 | 11/2009 | Wijesiriwardana |
| 2011/0094306 A1 | 4/2011 | Bratkovski et al. |
| 2012/0238890 A1 | 9/2012 | Baker et al. |
| 2013/0041272 A1 | 2/2013 | Arredondo et al. |
| 2013/0066168 A1 | 3/2013 | Yang et al. |
| 2014/0298667 A1 | 10/2014 | Alkhalaf |
| 2014/0336538 A1 | 11/2014 | Simonsen et al. |
| 2015/0250420 A1* | 9/2015 | Longinotti-Buitoni ..................... A61B 5/6804 600/301 |
| 2015/0342266 A1 | 12/2015 | Cooper et al. |
| 2015/0366504 A1* | 12/2015 | Connor ................ A61B 5/6804 600/301 |
| 2016/0242646 A1 | 8/2016 | Obma |
| 2016/0270700 A1 | 9/2016 | Baxi et al. |
| 2016/0338644 A1 | 11/2016 | Connor |
| 2017/0128000 A1 | 5/2017 | Martin et al. |
| 2017/0312576 A1* | 11/2017 | Natarajan ............. A61B 5/1118 |

OTHER PUBLICATIONS

International Search Report dated May 4, 2018 for PCT/US2018/014433.

Kibler, W. B., Ludewig, P. M., McClure, P. W., Michener, L. A., Bak, K., & Sciascia, A. D. (2013). Clinical implications of scapular dyskinesis in shoulder injury: the 2013 consensus statement from the 'Scapular Summit'. Br J Sports Med, 47(14), 877-885.

Postacchini, R., & Carbone, S. (2013). Scapular dyskinesis: Diagnosis and treatment. OA Musculoskeletal Medicine, 1(2), 20.

\* cited by examiner

# BODY PART MOTION ANALYSIS WITH WEARABLE SENSORS

RELATED APPLICATIONS

This application claims the benefit of U.S. provisional patent application "Body Part Motion Analysis with Wearable Sensors" Ser. No. 62/513,746, filed Jun. 1, 2017.

This application is also a continuation-in-part of U.S. patent application "Body Part Deformation Analysis Using Wearable Body Sensors" Ser. No. 15/875,311, filed Jan. 19, 2018, which claims the benefit of U.S. provisional patent applications "Body Part Deformation Analysis with Wearable Body Sensors" Ser. No. 62/448,525, filed Jan. 20, 2017, "Body Part Deformation Analysis using Wearable Body Sensors" Ser. No. 62/464,443, filed Feb. 28, 2017, and "Body Part Motion Analysis with Wearable Sensors" Ser. No. 62/513,746, filed Jun. 1, 2017.

Each of the foregoing applications is hereby incorporated by reference in its entirety.

FIELD OF ART

This application relates generally to motion analysis, and more particularly to body part motion analysis with wearable sensors.

BACKGROUND

The accurate measurement of the motion and deformation of a given shape has many applications, such as in the fields of machine vision, industrial automation, scientific biomechanics research, medical treatment, and 3D animation among others. The shapes whose deformation, movement, and motion are measured include objects of interest, manufactured parts, body parts, etc. The measurements can be used for object differentiation, where the object differentiation is based on material, size, shape, and cost, among many other parameters. When the shape being measured is a portion of a body such as the human body, then shape measurement has further applications in industries such as sports, healthcare, and 3D animation for entertainment and gaming. Accurate measurement can be used to obtain data related to personal medical information and to design medical treatments. Proper medical treatments are essential for comfort, safety, and therapeutic outcomes.

In a clinical setting, accurate and precise human body measurements are difficult to obtain. To start with, consider a relatively simple, static, volumetric body part measurement, such as measuring the volume of fluid buildup in a limb caused by lymphedema. This is typically a manual process where a tape measure is often used by a clinical professional to make body measurements. First the limb is marked along a longitudinal axis using the tape measure and a marking pen. An appropriate gradation, say every 1 cm, is marked. Next, a transverse circumference is measured at every gradation and recorded. The transverse circumferential measurements are repeated along the desired length of the limb. At a subsequent clinical visit, say one week or one month later, the measurements are taken again. Total limb volume V can be approximated by assuming a step-wise linear series of cylindrical disks. The volume V can be expressed as the area A of each transverse cross-section (where $A=C^2/4\pi$, and where C is the measured circumference) times the height h of each gradation, and then summing all of the cylindrical disk volumes into the total volume. In this way, lymphedema progression and/or treatment effectiveness can be monitored.

Unfortunately, even though this is a relatively simple example involving a static measurement of a non-moving body part, the typical clinical approach is fraught with inconsistencies and opportunities for human error. A different person may be making the measurements. Inconsistent pressure may be applied when measuring the circumference. The tip of the marking pen can be several mm wide. Subtle limb shape changes, whether related to lymphedema or not, may greatly affect the accuracy of the estimated volumetric model calculation. Many such difficulties exist for making even this relatively simple static, body part measurement.

While making static body part measurements is very difficult, it is even more difficult to measure moving body parts, such as a joint. Body part joint movement is three-dimensional, and the movement happens in real-time, that is, non-static. By necessity, the body part joint is moving when a measurement needs to be taken. Body part joint measurements can involve different deformations along multiple axes. Multiple measurements of a repetitive motion may be required. Measurements may need to be made while the body part is under a load condition or under nominal conditions. All of these variables present an additional layer of variation that makes measurement difficult. Added to all that complexity is the fact that body part joints are connected to other body part joints, which further complicates measurement and analysis of shape motion and deformation. Accordingly, a great need exists to be able to accurately measure and analyze body part motion.

SUMMARY

Proper measurement is critical to analyzing the motion of a body part. Techniques are disclosed for body part motion analysis with wearable sensors. A first stretch sensor changes electrical characteristics as the first stretch sensor stretches. The first stretch sensor is attachable to a body part through a tape, a compression sleeve, or a strap. Tape can be applied to the body part, and the stretch sensor can be attached to the tape using hooks or snaps. The tape can be a specialized tape such as a physical therapy tape, surgical tape, therapeutic kinesiology tape, and so on. One or more strips of tape can be attached to the body part. The one or more strips of tape can be attached in various configurations. The body part can include one or more of a knee, shoulder, elbow, wrist, hand, finger, thumb, ankle, foot, toe, hip, torso, spine, arm, leg, neck, jaw, head, or back. A measuring sensor coupled to the first stretch sensor collects the changes in electrical characteristics by the first stretch sensor based on motion of the body part. Multiple stretch sensors can be applied to the body part. A communication unit, coupled to the sensor, provides information from the sensor on the changes in electrical characteristics by the first stretch sensor. The communication unit can provide information using wired and wireless techniques. An inertial measurement unit (IMU) can provide augmented information on the motion of the body part. Information from the measuring sensor and the augmented information from the IMU can be analyzed to provide muscle activation and deformation characteristics. A receiving unit can receive the information provided by the communication unit. The received information can be displayed.

A system for motion analysis comprising: a first stretch sensor wherein: the first stretch sensor varies electrical characteristics as the first stretch sensor stretches; and the first stretch sensor is attachable to a body part; a measuring sensor coupled to the first stretch sensor that collects changes in the electrical characteristics by the first stretch sensor based on motion of the body part; and a communication unit, coupled to the measuring sensor, that provides information from the measuring sensor on the changes in the electrical characteristics by the first stretch sensor. A processor-implemented method for motion analysis is disclosed comprising: measuring body motion using a device comprising: a first stretch sensor wherein: the first stretch sensor varies electrical characteristics as the first stretch sensor stretches; and the first stretch sensor is attachable to a body part; a measuring sensor coupled to the first stretch sensor that collects changes in the electrical characteristics by the first stretch sensor based on motion of the body part; and a communication unit, coupled to the measuring sensor, that provides information from the measuring sensor on the changes in the electrical characteristics by the first stretch sensor; and displaying results of the measuring of the body motion.

In embodiments, the evaluation of motion of the body part includes performing a symmetry evaluation. In other embodiments, the evaluation of motion of the body part includes performing a motion consistency evaluation. In yet other embodiments, the evaluation of motion of the body part comprises a fine granular motion evaluation. And in still other embodiments, the evaluation of motion of the body part includes evaluation of angle, force, or torque. In embodiments, evaluations provide information for medical, sport, therapeutic, diagnostic, rehabilitation, and training applications.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
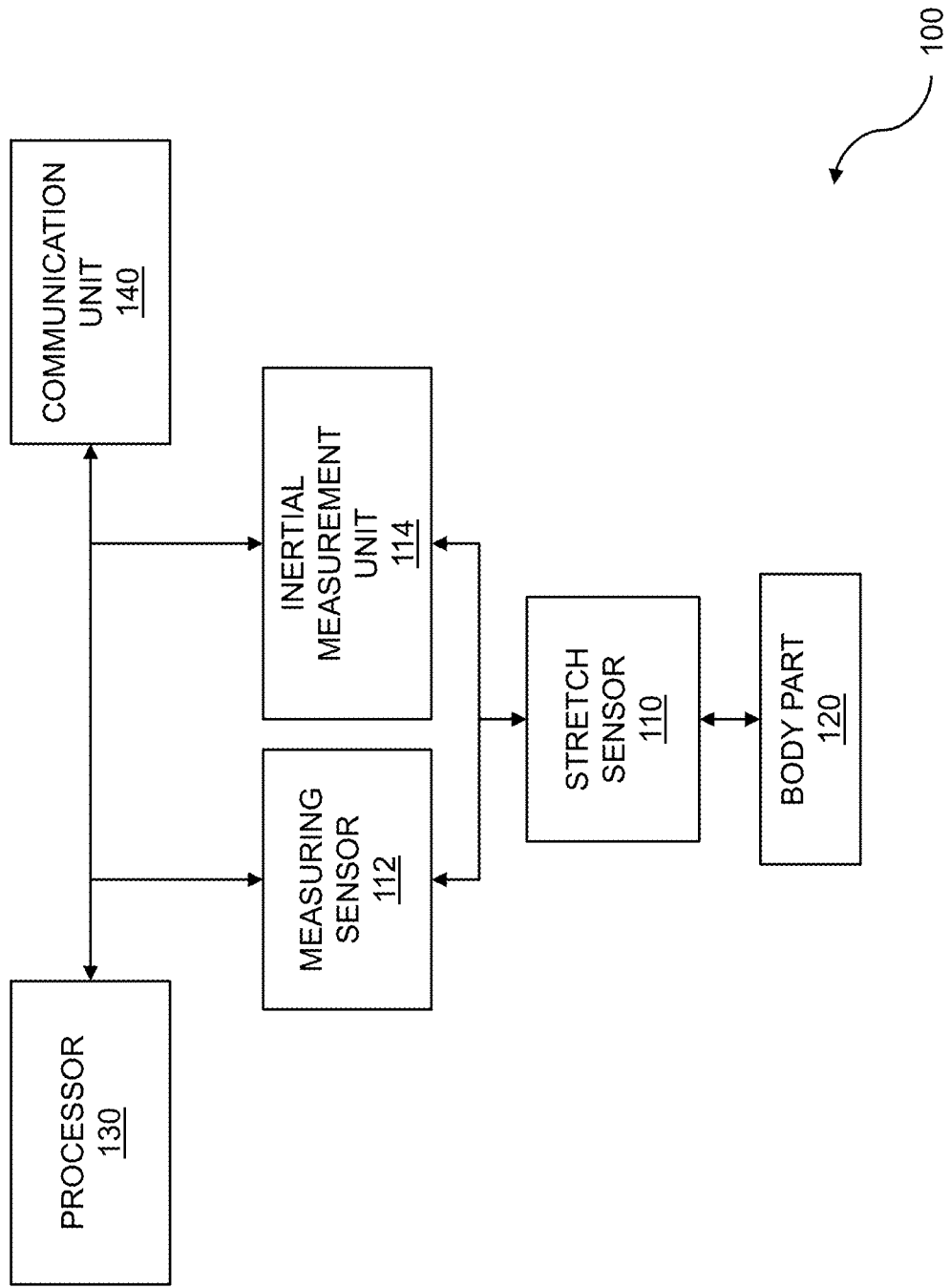
FIG. 1 is a system diagram for body part motion analysis with wearable sensors.

Techniques are disclosed for body part movement analysis with wearable sensors. The wearable sensors comprise stretch sensors for evaluating motion of a portion of the body. The wearable sensors can be attached to a fabric, which can be attached to a body part. The fabric can include tape, a woven fabric, a knitted fabric, a garment, etc. The tape can be a specialized tape such as a physical therapy tape, surgical tape, therapeutic kinesiology tape, and so on. The sensors can be used to measure various parameters relating to movement of the body part. The measurement of body part can be used to perform symmetry evaluation, to conduct movement consistency analysis over time, to evaluate a similar body part, to evaluate symmetrical operation of similar body parts, to perform fine granular motion evaluations, to evaluate angle, force and torque, etc. The body part can include one or more of a knee, shoulder, elbow, wrist, hand, finger, thumb, ankle, foot, toe, hip, torso, spine, arm, leg, neck, jaw, head, or back. The first stretch sensor changes electrical characteristics as the first stretch sensor stretches and typically detects linear displacement through stretching. As a sensor stretches, an angle of deformation can be determined for a portion of a body such as a knee or elbow. The electrical information can include changes in capacitance, resistance, impedance, inductance, etc.

A sensor coupled to the first stretch sensor collects the changes in electrical characteristics by the first stretch sensor based on motion of the body part. The sensor collects changes in capacitance, resistance, impedance, inductance, and so on. Information from the sensor can be augmented with inertial measurement unit (IMU) information. A communication unit, coupled to the sensor, provides information from the sensor on the changes in electrical characteristics by the first stretch sensor. The information provided by the communication unit is received by a receiving unit, separate from the first electroactive polymer, the sensor, and the communication unit. A display shows motion of the body part based on the information that was received by the receiving unit. The display can show an animation of the body part based on the motion of the body part based on the changes in electrical characteristics by the first stretch sensor. In embodiments, the body part is displayed in a context of an overall body of which the body part is a portion.

Traditional inertial measurement unit based systems attempt to infer the "absolute" location of a certain point of interest by integrating the acceleration reading in a 3D space. However, the accuracy of such an approach is limited by the sampling rate and the accuracy of the on-board accelerometer. One problem that is encountered by IMU-based solutions is called drift. Drift is the error (location distance) between the actual location of an object versus the location that is calculated/observed by the IMU reading. The drift error results from the accumulative error over time from the calculation. The approach taken here is based on measuring joint angle, where the angle is linear to the displacement reading of the stretch sensor. This approach does not suffer from the accumulative error. Body movement, or 3D motion of a body part, such as a hand gesture, can be accurately represented in a 3D space over time.

Disclosed techniques address sensing for motion tracking and motion analysis for motion tracking. In embodiments, tape such as physical therapy tape, therapeutic kinesiology tape, surgical tape, etc. can be applied to a body part. The body part can include one or more of a knee, shoulder, elbow, wrist, hand, finger, thumb, ankle, foot, toe, or hip, or other body parts such as torso, spine, arm, leg, neck, jaw, head, or back. One or more stretch sensors can be applied to the tape that is applied to a body part. The attaching of the one or more sensors to the tape can be accomplished using hooks, a hook and loop technique, fasteners, clips, bands, and so on. The one or more sensors that can be applied can provide an inferred joint angle movement based on absolute linear displacement of the one or more stretch sensors. The absolute linear displacement information can be augmented with information collected by an inertial measurement unit (IMU). The inertial measurement unit can include a six-axis or nine-axis IMU. The six-axis IMU can include a gyroscope for three axes, and an accelerometer for three axes. The nine-axis IMU can include a gyroscope for three axes, an accelerometer for three axes, and a magnetometer for an additional three axes. The addition of the magnetometer in the nine-axis IMU can improve accuracy. While the gyroscope and accelerometer can provide information about acceleration and rotation, their accuracy to measure location decreases over time due to drift. The information provided by the magnetometer can provide additional absolute direction sensing. The magnetometer measurements can be used to compensate for the drift over a time interval.

Techniques for motion analysis can be used for motion tracking. The motion tracking can include tracking body parts and the body parts are moved. The movement of the body parts can be related to tracking body part motion, body part test, body part therapy, and so on. The motion analysis can include acceleration and orientation information. The acceleration and orientation information relating to a body part can be collected by a six-axis or a nine-axis inertial measurement unit (IMU). The six-axis IMU can include acceleration and rotation, and the nine-axis IMU can include acceleration, rotation, and absolute direction information. A stretch sensor can be used to determine motion. The stretch sensor does not include an error due to drift and can be used to determine an angle and sagittal plane flexion and/or extension motion of a body part. The stretch sensor can include an electroactive polymer. More than one stretch sensor may be used. An additional stretch sensor can be attached at a right angle with respect to the first stretch sensor. The addition of the additional stretch sensor can be used to determine muscle function. The muscle function can include muscle stretch, muscle angle, muscle bulge, and so on. The information from the measuring sensor and the augmented information from the IMU can be analyzed to provide muscle activation and deformation characteristics. The muscle activation can comprise timing and displacement of muscle deformation.

A body part motion may be analyzed as part of a kinematic sequence, that is, as part of all of the body part component motions combined into a body movement. For example, a baseball pitcher delivering a fastball is a complex kinematic sequence made up of many complex body part motions. The movement of the body part motions can be both linear and rotational. Both the linear and rotational movements can be in three dimensions spatially, as well as being defined in the time dimension. The change in each body part's position in space can be captured in linear and rotational motion. Therefore, these movements can be reported as linear or angular velocity or momentum. All movements can be characterized as having both a timing component and a magnitude component. Other metrics such as force and torque can be calculated to define stresses about an anatomical joint. The interaction of the body parts and patterns displayed can be captured and analyzed. Body part motion can be broken into various, related time slices called phases. Phases can be further analyzed, categorized, and recognized for medical, sport, therapeutic, diagnostic, rehabilitation, and training applications, to name just a few. Body part motion and phases can be used to identify a high-fidelity understanding of body part motion microexpressions, which represent detailed muscle movements and timing analyses that can be extremely useful for understanding muscle performance, neuromuscular control, injury, rehabilitation, sport usage, training, and so on.

FIG. 1 is a system diagram for body part motion analysis with wearable sensors. Body part motion analysis is based on wearable sensors. A stretch sensor, which is attachable to a body part, changes electrical characteristics as it stretches. The stretch sensor can include an electroactive polymer or a flexible inductor. A sensor coupled to the stretch sensor collects the changes in electrical characteristics. A communication unit provides information to a receiving unit. The motion of the body part is displayed as an animation in a context of an overall body.

A system diagram for body part motion analysis with wearable sensors 100 is shown. The system diagram 100 includes a stretch sensor 110. Tape can be attached to a body part and a first stretch sensor 110 can be attached to the tape. Connectors, hooks, snaps, Velcro™, and the like can be used to attach the first stretch sensor 110 to the tape. The stretch sensor can include an electroactive polymer. In some embodiments, the stretch sensor includes a capacitive, resistive, or inductive sensor. The tape can include physical therapy tape and therapeutic kinesiology tape, a woven material, etc. The body part 120 to which the stretch sensor is attached can include one or more of a knee, shoulder, elbow, wrist, hand, finger, thumb, ankle, foot, toe, hip, torso, spine, arm, leg, neck, jaw, head, back, and so on. The stretch sensor 110 can be coupled to a wearable measuring sensor 112. The wearable sensor 112 can include two or more body sensors. The wearable sensor can collect electrical information including capacitance, resistance, impedance, inductance, and so on. The stretch sensor 110 can be coupled to an inertial measurement unit (IMU) 114. The inertial measurement unit can capture movement information, attitude information, position information, etc. The measuring sensor 112 can be coupled to a processor 130. The processor 130 can be used for controlling the one or more wearable sensors, for collecting data from the wearable sensors, for analyzing data from the wearable sensors, and so on. The measuring sensor 112 can be coupled to a communication unit 140. The communication unit 140 can provide wired and/or wireless communications between the stretch sensor 110, measuring sensor 112, and/or inertial measurement unit 114, and a receiving unit (not show). The communication unit 140 can include Ethernet™, Bluetooth™ Wi-Fi, Zigbee™, infrared (IR), and other communications capabilities. The communication unit 140 can send information including movement information, attitude information, position information, and so on.

Figure 2:
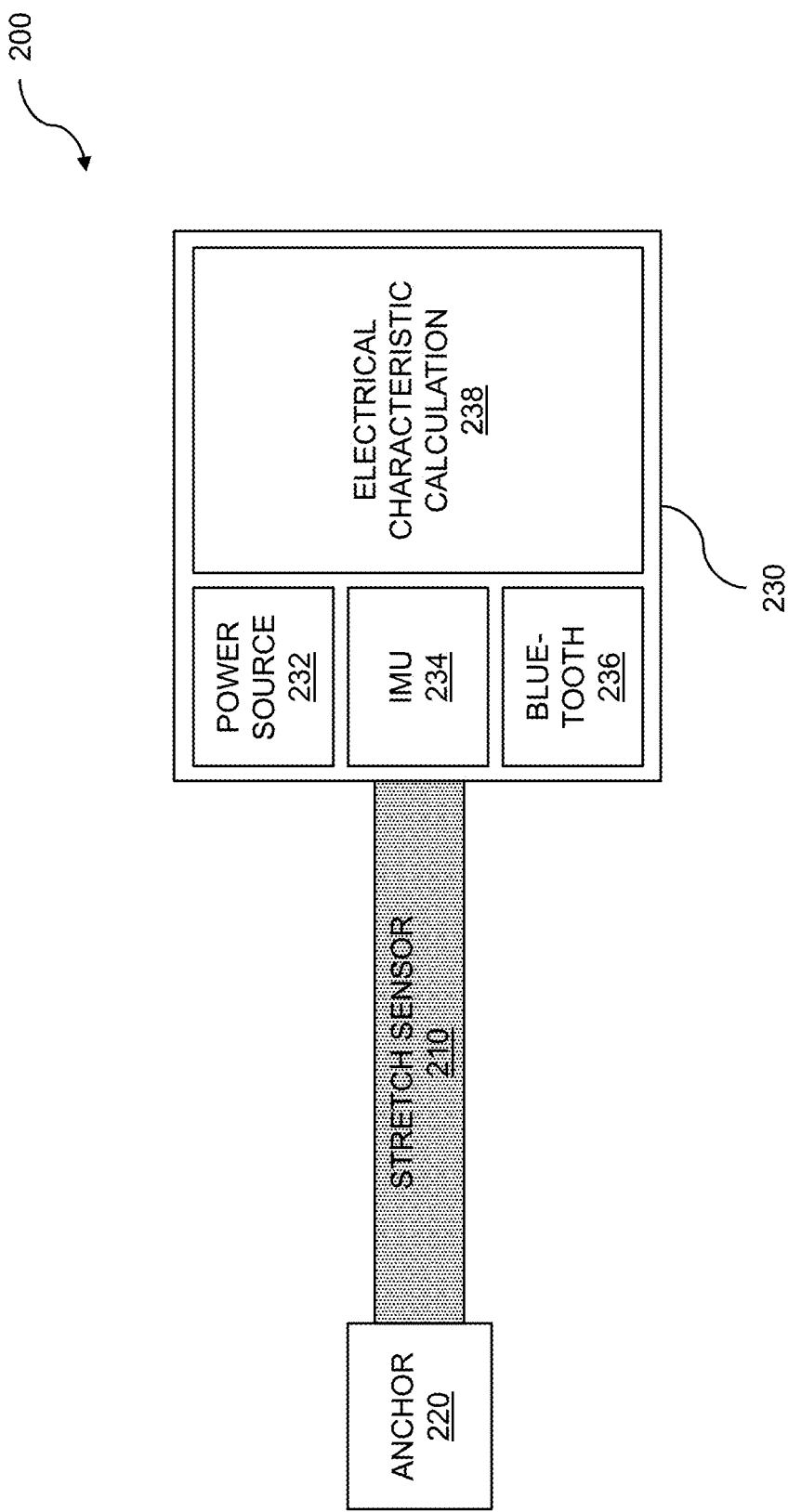
FIG. 2 illustrates an apparatus for attachment to tape on one or more body parts.

FIG. 2 illustrates an apparatus for attachment to tape on one or more body parts. Body part motion analysis can be based on wearable sensors. A stretch sensor changes electrical characteristics as it stretches, and the stretch sensor is attachable to a body part. A sensor coupled to the stretch sensor collects changes in electrical characteristics based on motion of the body part. A communication unit provides information from the sensor to a receiving unit. The information that is received is displayed. An apparatus for attachment to tape on one or more body parts 200 is shown. The apparatus includes a stretch sensor 210. While one stretch sensor is shown, other numbers of stretch sensor can be included. The stretch sensor can include an electroactive polymer. The stretch sensors can be configured in a variety of arrangements such as a t-shape, an offset-t-shape, a w-shape, an x-shape, a spider-shape, and so on. The stretch sensor 210 can be coupled to an anchor 220. The anchor can include hooks or other fasteners, and the anchor can be used to attach the stretch sensor to tape, fabric, and so on. When tape is used, the tape can be attached to the body part where the first stretch sensor can be attached to the tape.

In embodiments, the tape can include physical therapy tape. In other embodiments, the tape can include therapeutic kinesiology tape. The apparatus 200 can include an electrical component 230. The electrical component 230 can be coupled to the stretch sensor 210 and can collect changes in electrical characteristics of the stretch sensor 210. The electrical component 230 can include a power source 232 that can provide power to electrical circuits and can drive the stretch sensor 210. The electrical component can include an electrical characteristic calculation component 238 and an IMU 234. The electrical characteristic calculation component 238 can be used to determine stretch, bulge, displacement, and other physical characteristics based on body part motion. The electrical characteristic calculation component 238 can be used to determine muscle activation and deformation. Muscle activation includes timing and displacement of muscle deformation, and subtle muscle activation analysis can characterize muscle microexpression, which represents detailed muscle movement and timing analysis that can be extremely useful for understanding muscle performance, neuromuscular control, injury, rehabilitation, sport usage, training, and so on. Muscle microexpression is not detectable by image-based muscle observation, nor is it detectable by IMU-based muscle observation alone, nor is it detectable by a combination of the two.

Movement patterns can include body part movements (e.g., a forearm), body segment movements (e.g., an entire arm), and full body movement patterns (e.g., a golf swing). Muscle contraction movement output magnitudes can be part of a kinematic sequence. The components can be expressed in terms of both magnitude and timing. All of the components can be analyzed, calculated, or inferred by the electrical characteristic calculation component 238. The electrical component 230 can include a Bluetooth™ communication unit 236 which can be used to send collected changes in electrical characteristics of the stretch sensor 210 and IMU 234 to a receiving unit (not shown). Alternatively, the electrical characteristic calculation component 238 can provide a muscle microexpression summary analysis using Bluetooth™ communication unit 236.

Figure 3A:
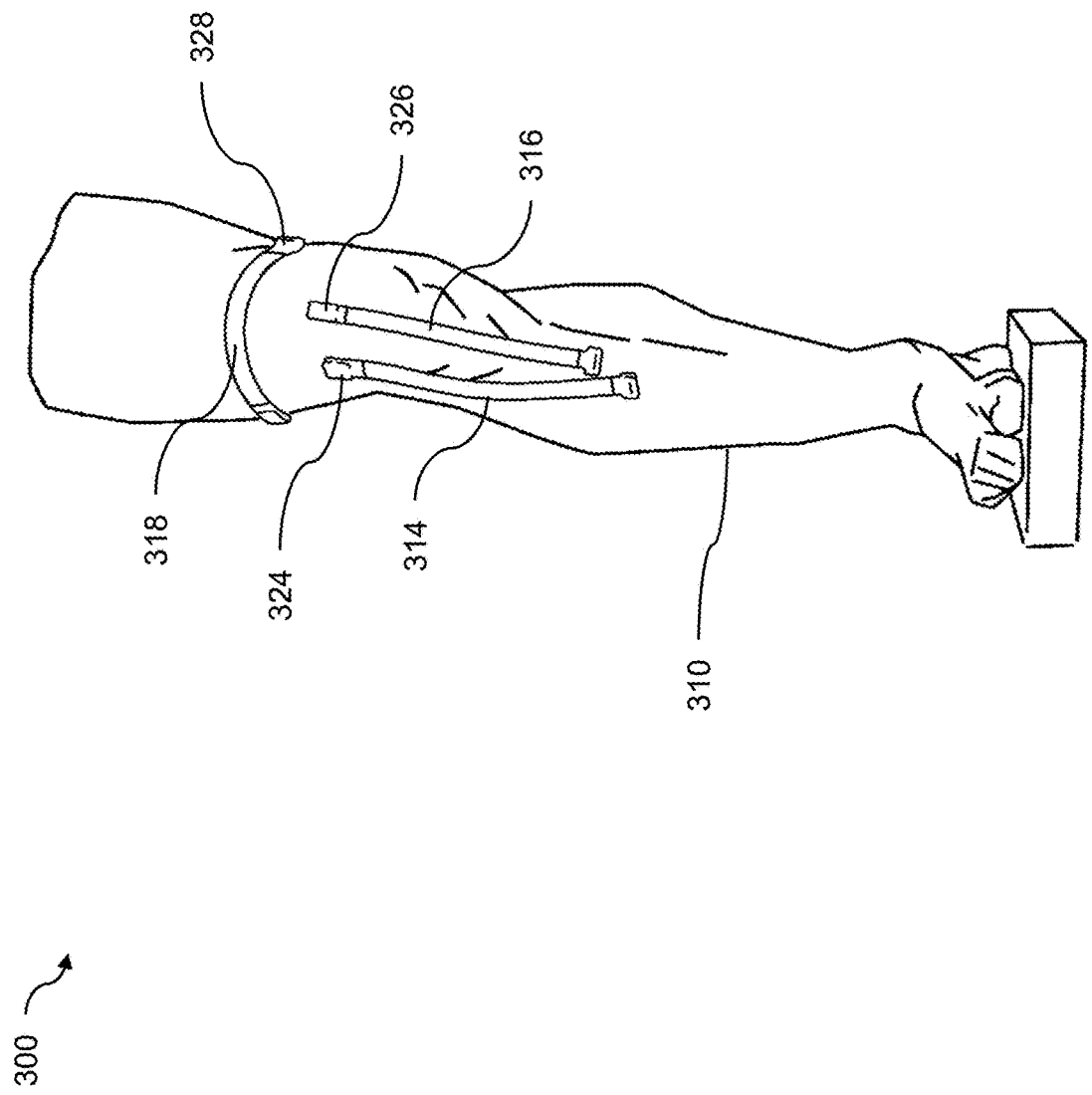
FIG. 3A shows stretch sensor configurations for a leg.

FIG. 3A shows stretch sensor configurations for a knee. Body part motion analysis uses wearable sensors, where the wearable sensors can include stretch sensors. A first stretch sensor, which changes electrical characteristics as the stretch sensor stretches, can be attachable to a body part. A sensor can be coupled to the first stretch sensor and can collect changes in electrical characteristics based on motion of the body part. A communication unit can provide information to a receiving unit from the sensor on the changes in electrical characteristics by the first stretch sensor. A display can show motion of the body part based on the received information. The display can show an animation of the body part, and the body part can be displayed in a context of an overall body.

A stretch sensor configuration for a leg is shown 300. Multiple stretch sensors can be attached using tape (not shown) to a leg 310 in various configurations including both longitudinal and transverse attachments. The tape that can be applied to the body part can include physical therapy tape, therapeutic kinesiology tape, surgical tape, and so on. Stretch sensor networks, such as 314, 316, and 318 can be attached to a body part such as a knee or thigh. Knee stretch sensor networks 314 and 316 are shown in a longitudinal configuration, while thigh stretch sensor network 318 is shown in a transverse configuration. Sensors 314, 316, and 318 can be coupled to electronic components 324, 326, and 328, respectively. Tape strips attached to the body parts (not shown) can be used to anchor sensors 314, 316, and 318 at either end, wherein one of the ends contains the electronic components as just described. The stretch sensor networks 314, 316, and 318 can each be coupled to a receiving unit (not shown) using a communications unit within electrical components 324, 326, and 328, respectively. Other sensor and tape configurations are possible, such as a w-shape, a t-shape, an l-shape, an x-shape, a star-shape, a hand-shape, a z-shape, and so on.

Application various sensor and tape configurations to a body part such as a knee can be used to determine angle measurements for the knee on which the tape is applied. In embodiments, angle measurements can include sagittal plane flexion and extension. In addition to angle measurements for a given body part, muscle function assessment can also be performed. In embodiments, muscle function assessment can include displacement of muscle contraction that can occur during an activity. The activity can include normal physical activity such as walking, and strenuous physical activity such as running, cycling, sports, and so on. Peak displacement of a muscle can be based on maximum contraction of key superficial muscle groups. A sensor can be attached to a targeted muscle group, over the location of greatest muscle mass displacement. In addition to peak muscle displacement for muscle function determination, an amount of time required to reach peak muscle contraction can be recorded. Other sensors can be applied to knee measurements. In embodiments, an inertial measurement unit (IMU) can be used to track acceleration and orientation of a body part such as a knee. Based on measurement collected from the IMU, intersegmental movement can provide information on movement patterns across anatomical joints. The information based on the intersegmental movement provides information on a fluidity of movement and a quality of motion. This information can provide side to side comparison of movement of the anatomical joints for healthy populations in contrast with injured populations.

Figure 3B:
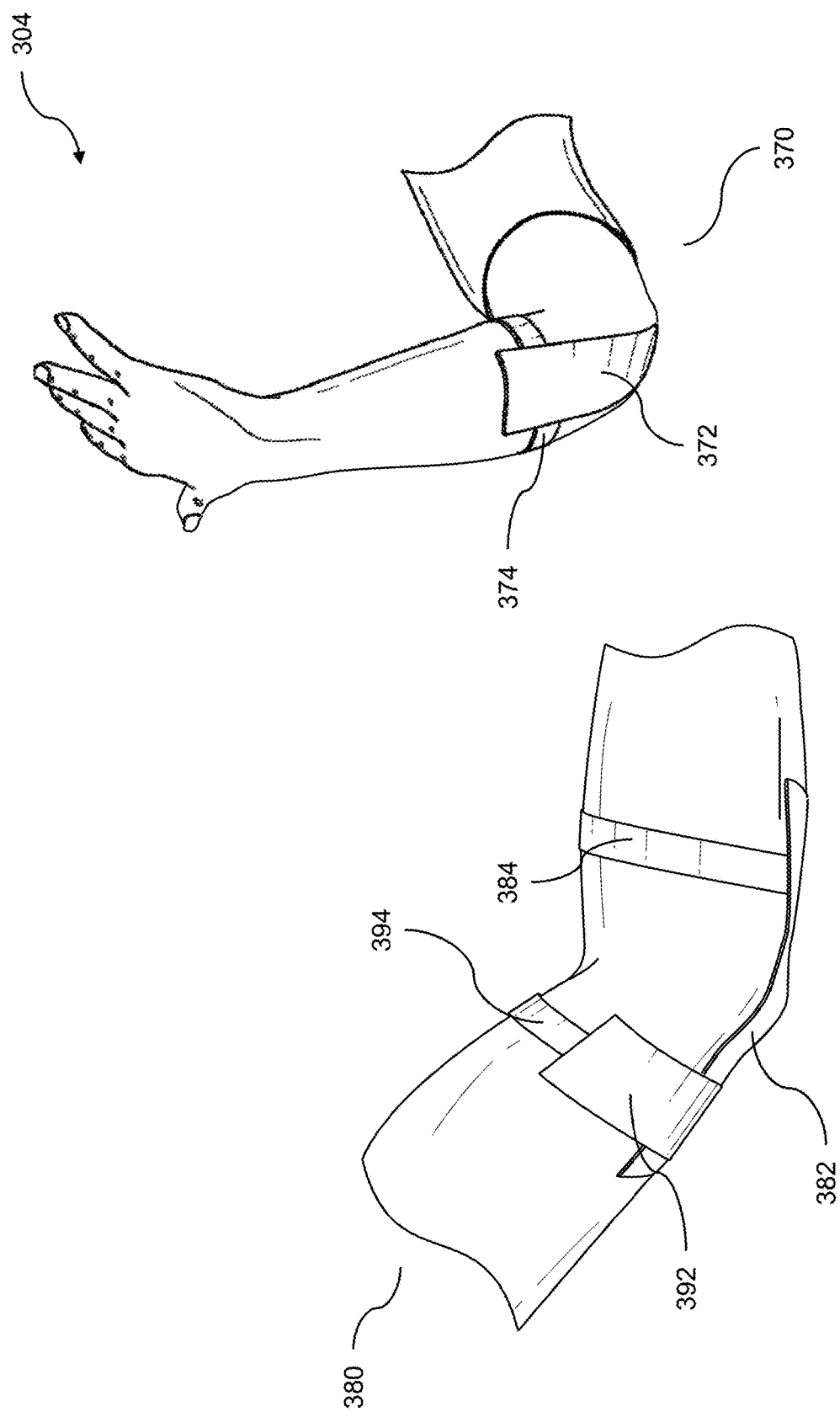
FIG. 3B shows stretch sensor configuration for an arm.

FIG. 3B shows stretch sensor configuration for an arm. Wearable stretch sensors are used to analyze body part motion. A stretch sensor can be attached to a body part such as an elbow. Stretching of the stretch sensor by moving the elbow can change electrical characteristics of the sensor. A sensor can be used to collect the changes in electrical characteristics, and a communication unit can be used to provide information from the sensor to a receiving unit. The received data can be displayed, where the display can include an animation of the body part and a context of the body part in an overall body. Elbow, forearm, and tricep sensor and tape configurations 304 are shown. Elbow view 370 includes an elbow sensor 372 (shown pictorially) situated longitudinally along an elbow and forearm sensor 374 situated transversely across the upper forearm. Both sensor 372 and 374 can be anchored on tape. The tape can be combined or integrated with the sensors as may be practicable based on the exact configuration. For example, sensors 372 and 374 may have a common tape anchor point where they intersect.

Similarly, arm view 380 includes elbow sensor 382 along with forearm sensor 384, shown analogously to sensors 372 and 374 of elbow view 370. Additionally, arm view 380 includes bicep sensor 394 transversely situated on an upper arm and attached to tape 392. Both sensor 382 and sensor 394 can have a common tape anchor point where they intersect, depending on which muscle activation and deformation is desired for analysis. Sensors 372, 374, 382, 384, and 394 can include integrated electronic components (not shown) as described earlier. Sensors 372, 374, 382, 384, and 394 can also include attachment elements (not shown) as again described earlier. As the elbow and forearm shown in elbow view 370 and the elbow, forearm, and bicep shown in arm view 380 flex, connections to tape or other anchoring mechanism for sensors 372, 374, 382, 384, and 394 anchor the ends of the sensors, which causes the stretch sensor to change shape. The shape change(s) is sensed and sent to the communication unit(s). In embodiments, more than one stretch sensor can be applied to a body part. The added stretch sensor or sensors can be used to measure movement of the body part, muscle displacement, muscle bulge, and so on. The change or changes in shape of the stretch sensor cause changes in electrical characteristics of the stretch sensor. The changes in electrical characteristics of the stretch sensor can be collected and communicated to the receiving unit. The received information relating to elbow movement can be displayed.

An application of an offset-t-shape tape configuration as applied to a body part such as an elbow can be used to determine angle measures for the elbow. The angle measurements based on information collected from stretch sensors applied to the tape configuration can include sagittal plane flexion and extension motion. Muscle function can also be assessed, where muscle function can include muscle contraction. In embodiments, peak muscle displacement can be recorded during an active muscle contraction based on key superficial muscle groups. Muscle function assessment can include recording and comparing muscle contraction that occurs during demanding physical activities such as a sporting activity. Muscle function can include recording a greatest displacement for a muscle, and the elapsed time required to attain peak muscle contraction. An inertial measurement unit (IMU) can be used for measuring acceleration and orientation of one or more body parts. When the body part includes an elbow, the IMU can be used for measuring the acceleration and orientation of a forearm and arm segments. In embodiments, the IMU can be used to measure intersegmental movement of a body part. The intersegmental movement determination can be used to provide information on movement patterns of anatomical joints such as knees, elbows, hips, shoulders, wrists, ankles, etc. The anatomical joint movement pattern information can be used to determine fluidity of body part movement over time and from side to side. Anatomical joint movement comparison can be used to compare the body parts of healthy versus injured populations.

Figure 4:
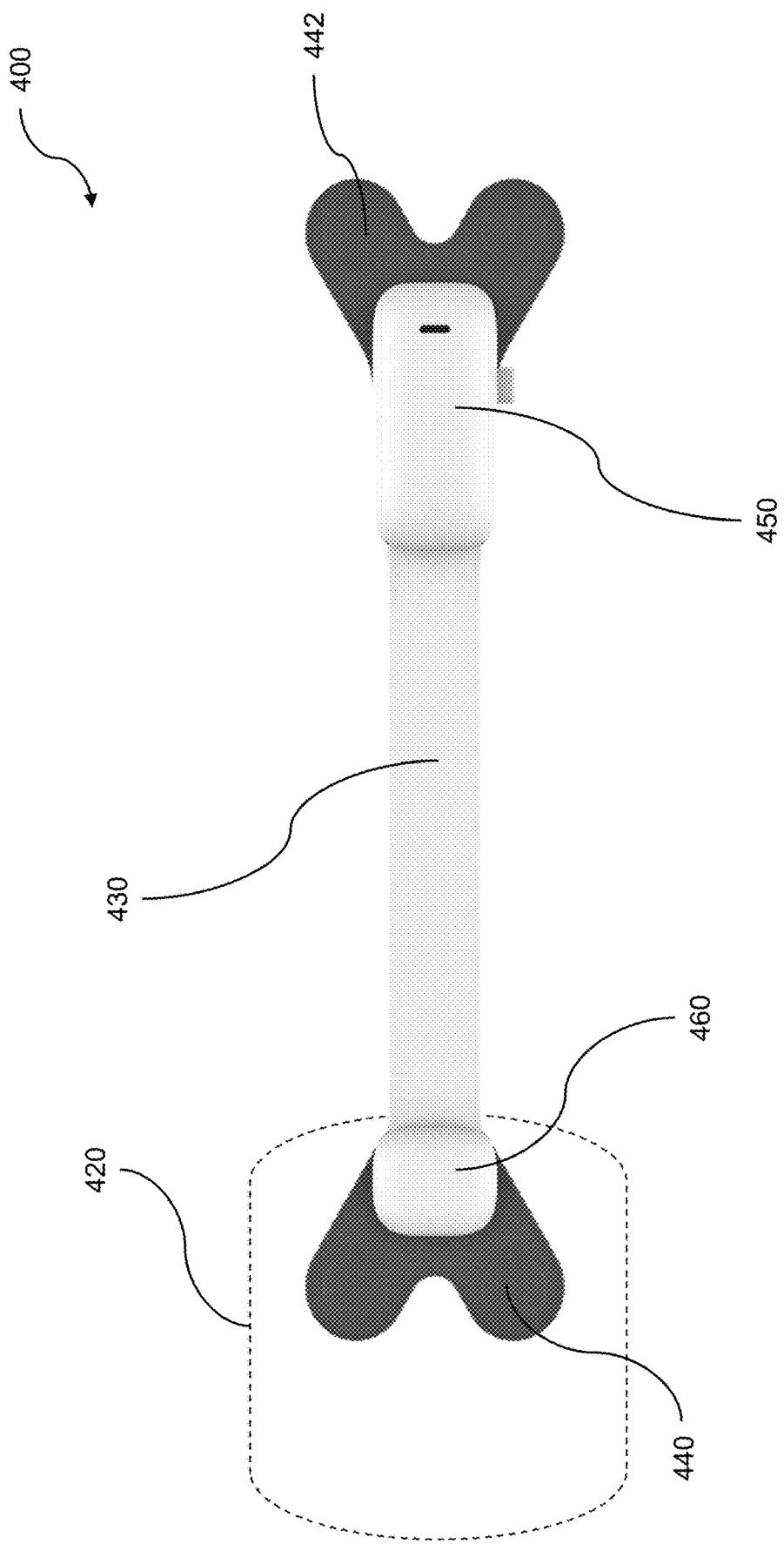
FIG. 4 shows a representative diagram of sensor and tape.

FIG. 4 shows a representative diagram of sensor and tape 400. Wearable sensors based on stretch sensors are used for body part motion analysis. The stretch sensor changes electrical characteristics as it stretches, and the stretch sensor is attachable to a body part. A sensor coupled to the stretch sensor collects changes in electrical characteristics based on body part motion. A communication unit provides information from the sensor to a receiving unit. The information that is received is displayed. The display shows an animation of the body part. The body part is displayed in a context of an overall body. A representative diagram of stretch sensors and tape 400 is shown. Tape 420, such as physical therapy tape or therapeutic kinesiology tape can be attached to a body part. Anchoring tape can take many forms and shapes as indicated by the dotted outline of tape 420. The body part can include one or more of a knee, shoulder, elbow, wrist, hand, finger, thumb, ankle, foot, toe, hip, torso, spine, arm, leg, neck, jaw, head, back, and so on. One or more stretch sensors can be included. Stretch sensor 430 can be attached to the tape 420 using anchors 440 and 442. The anchors can include hooks, snaps, adhesive, and so on. A cover 450 can cover an electrical component where a measuring sensor can reside that is coupled to the stretch sensor. The electrical component can include a power supply, a communication unit, an IMU, an electrical characteristic processing unit, etc. Various configurations of sensor and tape are possible. Multiple sensors can be attached to a single tape or multiple tapes. Similarly, a single sensor can be attached to multiple tapes. The underside of sensor end 460, and on the other end of sensor 430, communication unit 450, can include hooks, snaps, adhesive, and so on, to attach to tape attached to a body part, such as tape 420.

Figure 5:
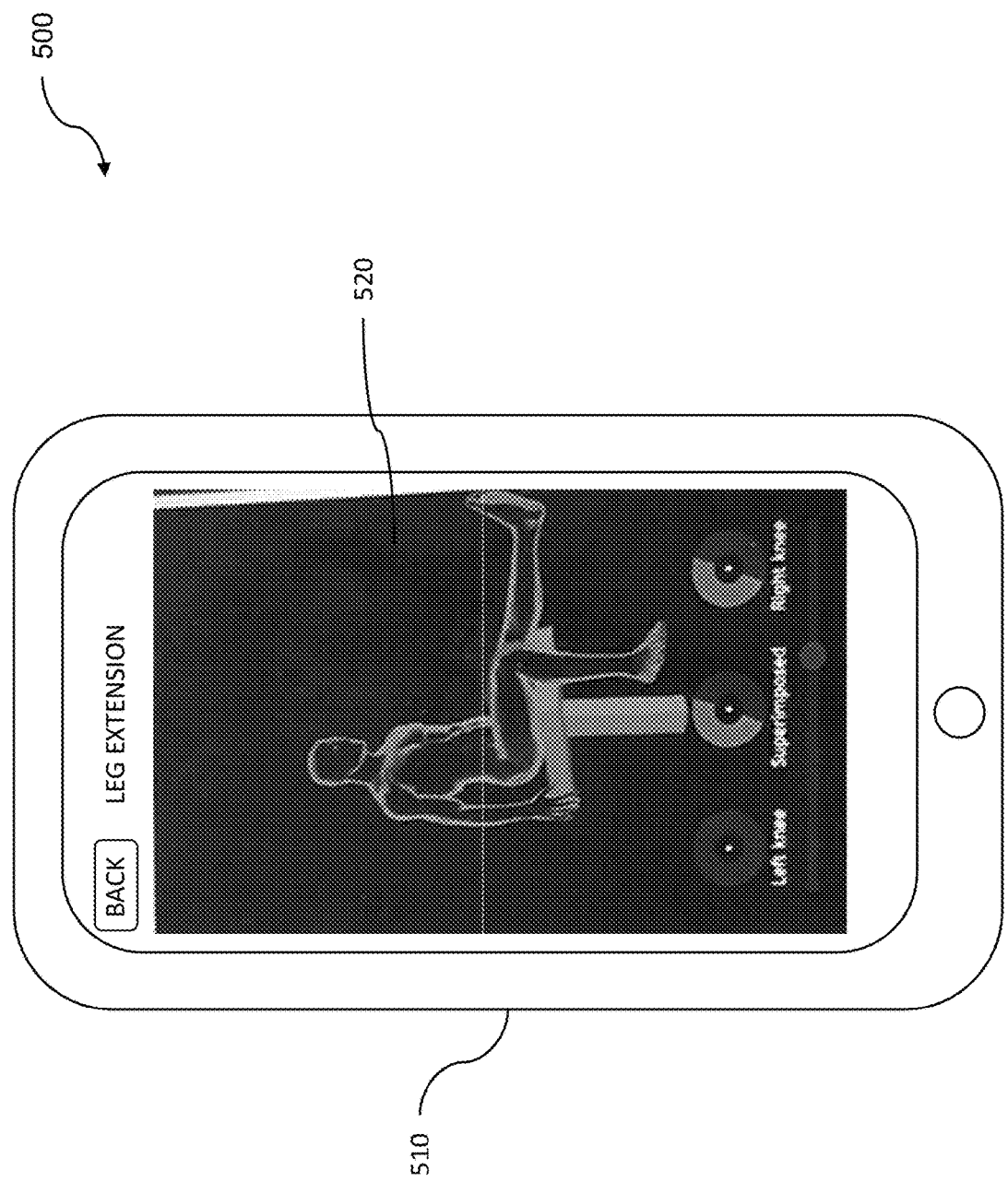
FIG. 5 illustrates leg extension with sensor evaluation.

FIG. 5 illustrates leg extension with sensor evaluation. Body part motion analysis is based on body-wearable stretch sensors. The stretch sensors can include electroactive polymer sensors. A stretch sensor changes electrical characteristics as the stretch sensor stretches. A sensor coupled to the stretch sensor collects changes in electrical characteristics based on motion of the body part. A communication unit provides sensor information to a receiving unit. The information is displayed based on an animation of the body part. The body part is displayed in a context of an overall body. Leg extension and sensor evaluation is shown 500. A display 520 can be coupled to an electronic device 510, where the electronic device can be a smartphone, a personal digital assistant (PDA), a tablet, a laptop computer, and so on. Changes in electrical characteristics by a stretch sensor can be rendered, along with an animation on the display 520. The animation can include a human body, a body part of the human body, and so on. In 500, an animation of the human body with the left leg extended is shown. Sensor evaluation data can be shown with the animation of the body, separate from the animation of the body, and so on. The sensor evaluation can include evaluation of body joints such as the knee. The sensor evaluation can include left knee flex, right knee flex, superimposed knee flex, and so on. The superimposed flex view can be used to compare body symmetry and body symmetric performance. For example, a left knee that has been injured and undergoing rehabilitation can be compared to a right knee that was not injured. Furthermore, the sensor evaluation can be used to predict injury potential or injury probability based on symmetrical evaluation or muscle deformation analysis over time. The display 520 can be part of an overall evaluation toolkit that can be useful for understanding muscle performance, neuromuscular control, injury, rehabilitation, sport usage, training, and so on.

Figure 6:
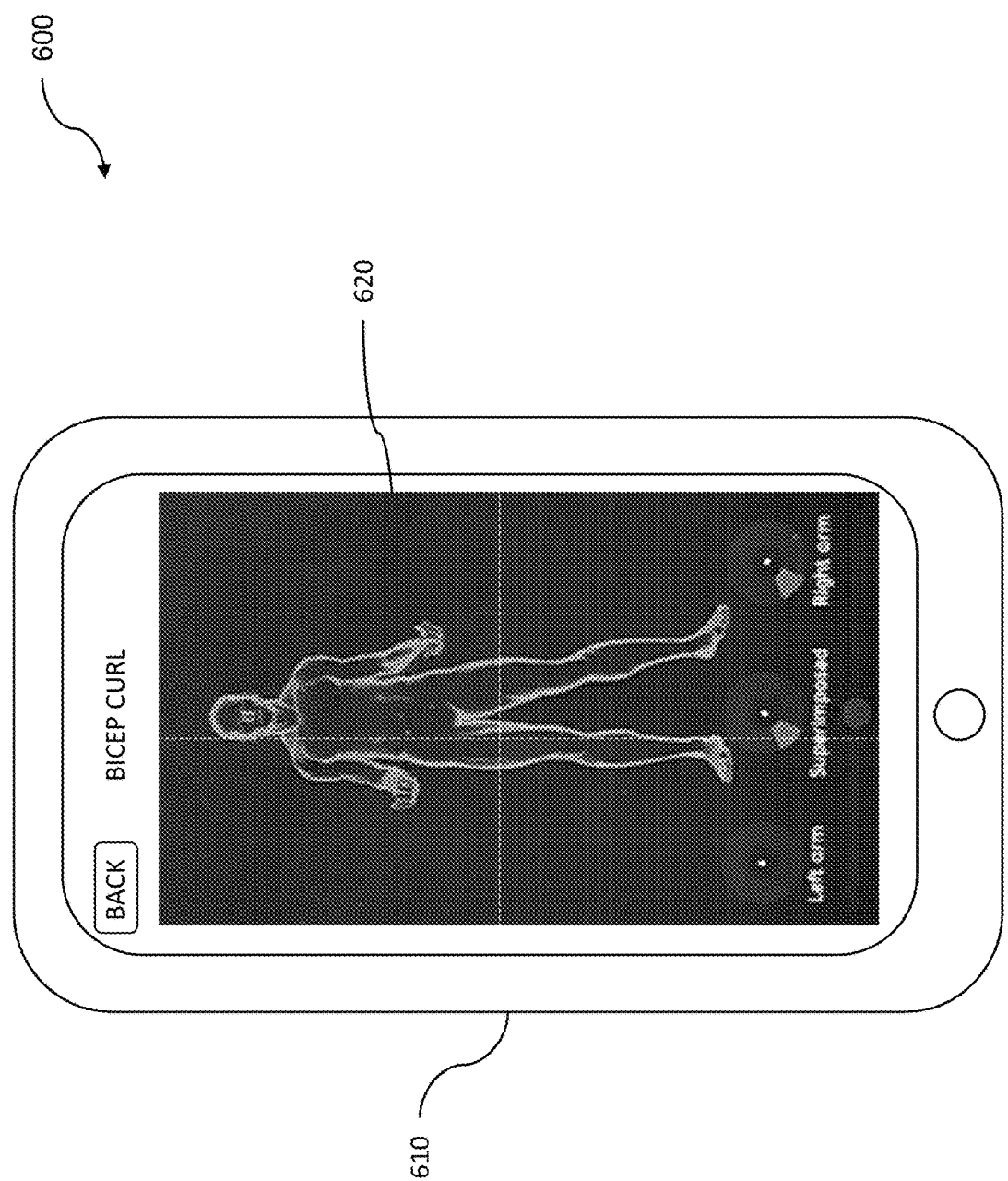
FIG. 6 shows bicep curl with sensor evaluation.

FIG. 6 shows bicep curl with sensor evaluation. Body part motion analysis uses wearable stretch sensors. A stretch sensor is attachable to a body part and changes electrical characteristics as the electroactive polymer stretches. A sensor coupled to the stretch sensor collects changes in electrical characteristics based on motion of the body part. A communication unit provides sensor information to a receiving unit. The information that is received is displayed based on an animation of the body part. The body part is displayed in a context of an overall body. Bicep curl and sensor evaluation 600 is shown as an animation. A display 620 can be coupled to an electronic device 610 such as a smartphone, a personal digital assistant (PDA), a tablet, a laptop computer, etc. Changes in electrical characteristics by a stretch sensor can be rendered along with an animation on the display 620 coupled to the device 610. The animation can include a human body, a body part of the human body, etc. An animation of the human body with bicep curl is shown. Sensor evaluation data can be shown with the animation of the body, separate from the animation of the body, and so on. The sensor evaluation can include evaluation of body limbs such as arms. The sensor evaluation can include the left arm, right arm, superimposed arm motion, etc. The display 620 can be part of an overall evaluation toolkit that can be useful for understanding muscle performance, neuromuscular control, injury, rehabilitation, sport usage, training, and so on.

Figure 7:
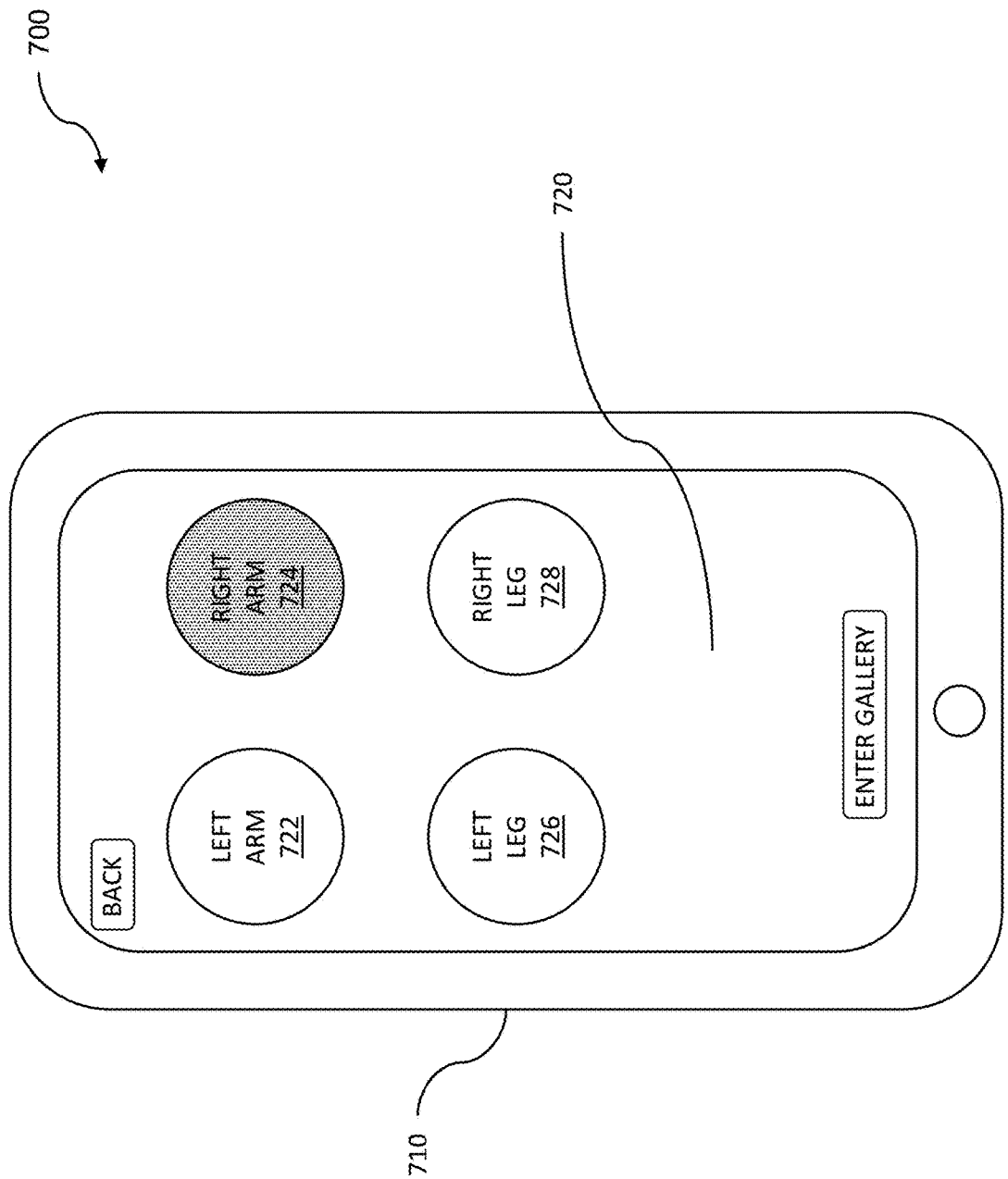
FIG. 7 illustrates limb selection graphical user interface.

FIG. 7 illustrates a limb selection graphical user interface 700. Wearable sensors can be used to analyze body part motion. Tape can be applied to the body part and a stretch sensor can be attached to the tape using hooks. The stretch sensor can change electrical characteristics as it stretches. A sensor coupled to the stretch sensor can collect changes in electrical characteristics based on motion of the body part. A communication unit can provide information from the sensor to a receiving unit. Motion of the body part can be shown on a display. The displayed body part can be an animation and can be displayed in the context of an overall body. A graphical user interface (GUI) for limb selection 700 is shown. The GUI can be rendered on a display 720 coupled to an electronic device 710. The electronic device can include a smart phone, a personal digital assistant (PDA), a tablet, a laptop computer, or other electronic device coupled to a display. The selection GUI enables a user to select a limb of interest, to observe information related to the limb, to initiate data collection for a test of a limb, and so on. The GUI includes selection icons including left arm button 722, right arm button 724, left leg button 726, and right leg button 728. Button 724 is shaded to show selection. In other embodiments, the selection GUI could include buttons for other body parts such as knees, neck, elbows, hips, back, shoulders, and so on. The GUI 700 can be part of an overall evaluation toolkit that can be useful for understanding muscle performance, neuromuscular control, injury, rehabilitation, sport usage, training, and so on.

Figure 8:
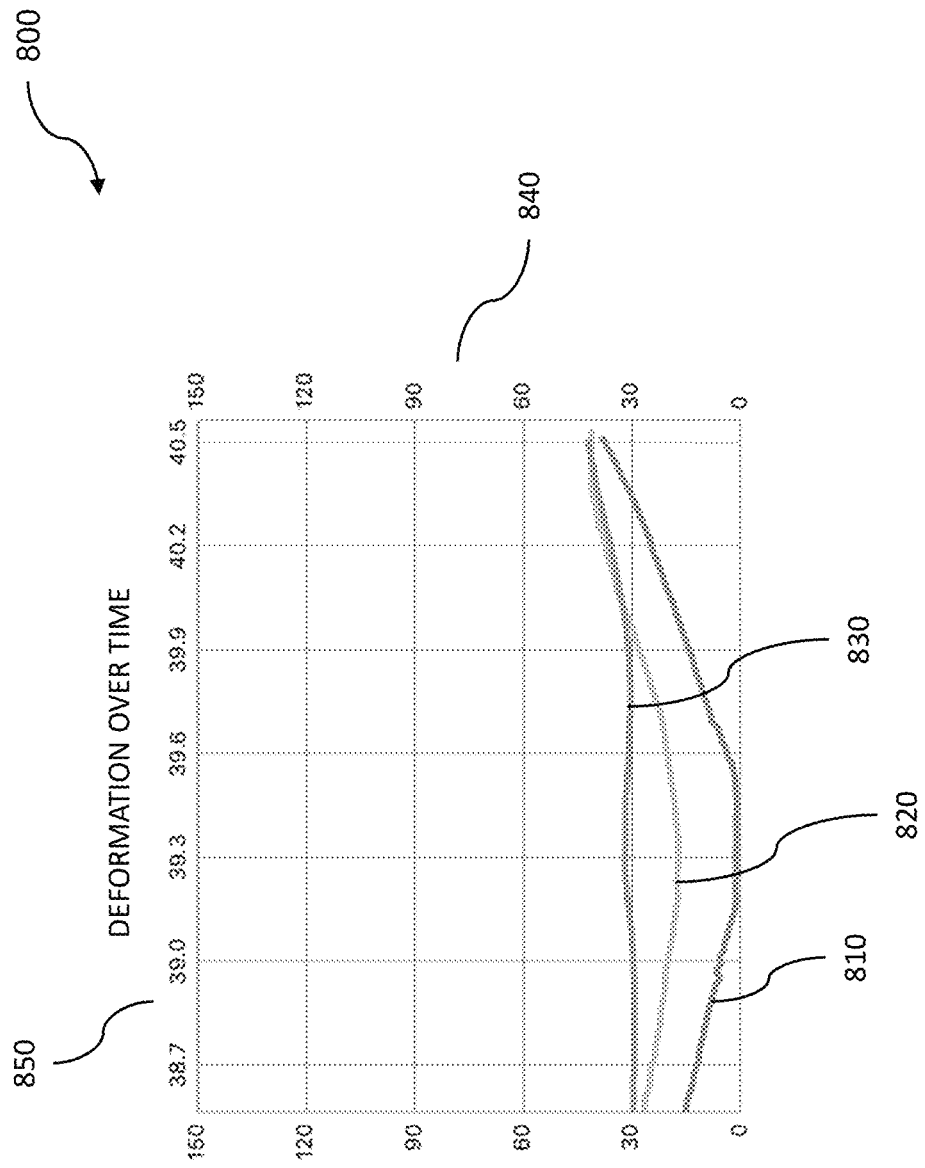
FIG. 8 shows line graph response of stretch sensor results.

FIG. 8 shows line graph response of stretch sensor results. Body part motion analysis is based on wearable sensors. A wearable sensor can include an electroactive polymer sensor. A stretch sensor, which is attachable to a body part, changes electrical characteristics as it stretches. A sensor coupled to the stretch sensor collects the changes in electrical characteristics. A communication unit provides information to a receiving unit. The motion of the body part is displayed as an animation in a context of an overall body. Line graph response of stretch sensor results 800 is shown. A line graph can be rendered on a display coupled to an electronic device such as a smart phone, a personal digital assistant (PDA), a tablet, a laptop computer, or other electronic display. The line graph can be based on changes in electrical characteristics by the stretch sensor based on motion of the body part. The electrical characteristics can include resistance, capacitance, inductance, reactance, and so on. The changes in electrical characteristics can be mapped to linear displacement in Metric or English units, angular displacement, in degrees or radians, etc. The line graph response of stretch sensor results 800 can include multiple analyzed sensor measurements showing deformation as a function of time. Lines 810, 820, and 830, for example, show various and varying amounts and rates of deformation on the y-axis 840 across a time interval on the x-axis 850. The amount and rate of lines 810, 820, and 830 can correspond to body part muscle motion analysis based on wearable sensors.

Figure 9:
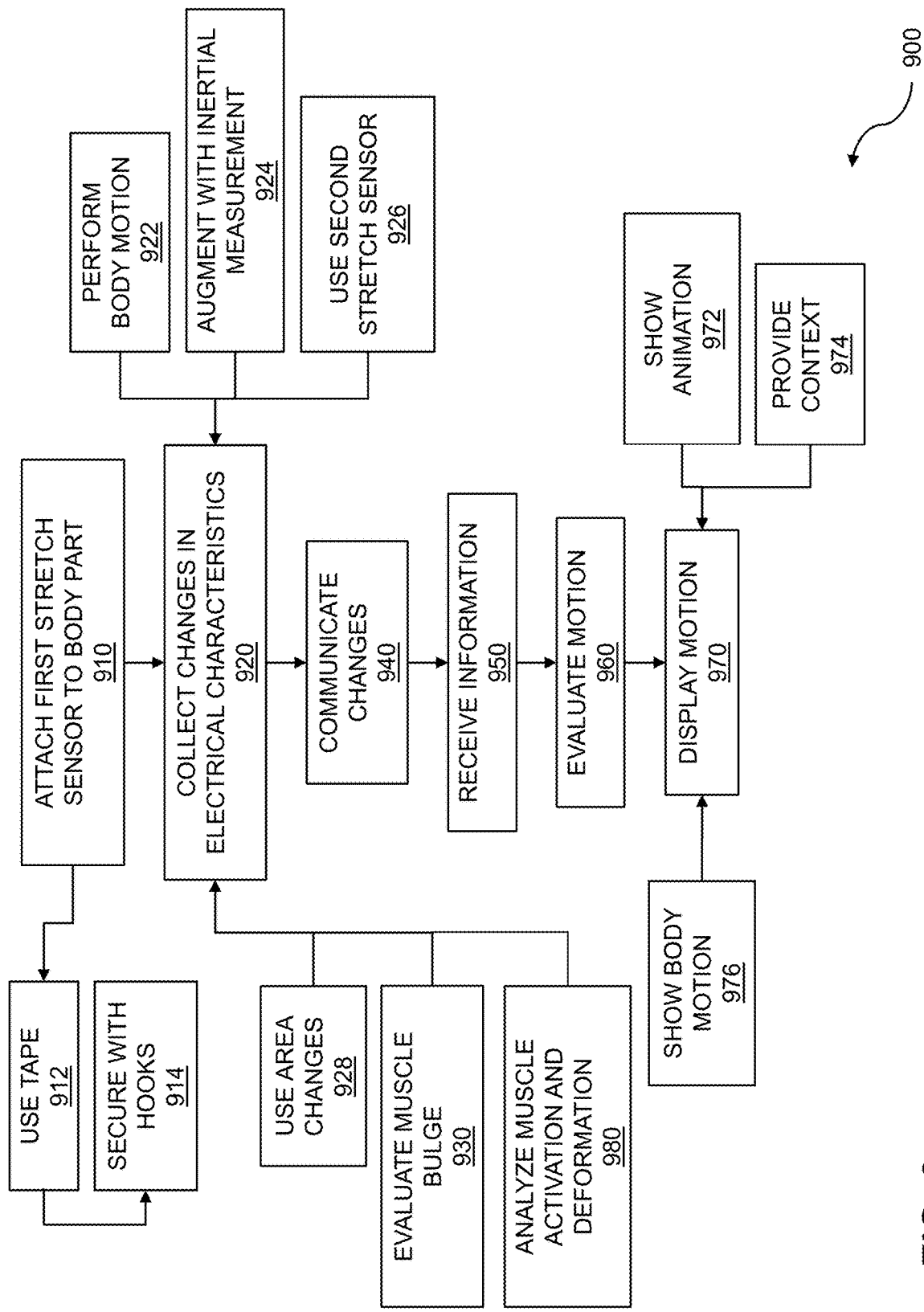
FIG. 9 is a flow diagram for body motion sensor usage.

FIG. 9 is a flow diagram for body motion sensor usage. Body-wearable sensors are used for body part motion analysis. A stretch sensor, which changes electrical characteristics as it stretches, is attachable to a body part. A sensor is coupled to the stretch sensor to collect the changes in electrical characteristics based on motion of the body part. A communication unit provides sensor information to a receiving unit. The received data can be displayed to show motion of the body part. The display can show an animation of the body part, and the body part can be displayed in a context of an overall body. The flow 900 includes attaching the first stretch sensor to a body part 910. The attaching of the first stretch sensor to the body part can be accomplished by placing the sensor on the body part, by surrounding the body part with the sensor, and so on. In embodiments, tape 912 can be attached to the body part, and the first stretch sensor can be attached to the tape. Various types of tape can be used to attach the first stretch sensor to the body part. In embodiments, the tape can include physical therapy tape. In other embodiments, the tape can include therapeutic kinesiology tape. Hooks 914 can be used to attach the first stretch sensor to the tape. The hooks can enable easy attachment of the stretch sensor to the tape, easy removal of the stretch sensor from the tape, etc.

The flow 900 includes collecting the changes in electrical characteristics 920 by the first stretch sensor based on motion of the body part. The electrical characteristics can include resistance, capacitance, impedance, and/or inductance. In embodiments, the first stretch sensor stretches in a single dimension. More than one stretch sensor can be attached to tape in order to stretch in multiple directions. The changes in electrical characteristics of the first stretch sensor can be based on performing body motion 922. The body motion can include raising an arm, extending a knee, and so on. The collecting changes in electrical characteristics can include an inertial measurement unit (IMU) that can augment information 924 on the motion of the body part. The IMU can measure linear displacement, angular displacement, magnetic field, and so on. The collecting changes in electrical characteristics can include a second stretch sensor 926, used for measuring motion of the body part, where the second stretch sensor can stretch in a single dimension that is substantially at a right angle to the first stretch sensor. While a first stretch sensor and a second stretch sensor are described, other configurations as described elsewhere can be used for body part motion analysis. The other configurations can include a t-shape, an l-shape, a w-shape, a star-shape, and so on. The collecting changes in electrical characteristics can include using area changes. In embodiments, the first stretch sensor can sense area changes 928 for the first stretch sensor to produce the changes in electrical characteristics. The area changes can include surface area, cross-sectional area, and so on. In embodiments, the first stretch sensor senses variations in muscle bulge 930 due to the changes in electrical characteristics. Embodiments include analyzing muscle activation and deformation 980.

The flow 900 includes communicating changes 940. The communicating changes can include using a communication unit, coupled to the sensor, that provides information from the sensor on the changes in electrical characteristics by the first stretch sensor. The communication unit can use wired and wireless protocols. Among the wireless protocols, the communication unit can use Bluetooth™, Wi-Fi, Zigbee™, infrared (IR), etc. The flow 900 includes receiving information 950. A receiving unit, separate from the first stretch sensor, the sensor, and the communication unit, can receive the information from the communication unit. The receiving unit can use the wired and wireless protocols used by the communication unit. The flow 900 includes evaluating motion 960. The evaluating of motion can be used to evaluate motion of the body part to which one or more stretch sensors are attached. The motion evaluation can be used to evaluate the function of a body part, the flexibility of the body part, the effectiveness of a therapy applied to the body part, and other motion-based evaluations. In embodiments, evaluation of motion of the body part can perform a symmetry evaluation. In other embodiments, the symmetry evaluation can include an evaluation of a similar body part. The symmetry evaluation can be used to evaluate symmetrical body parts such as shoulders, elbows, wrists, hips, knees, ankles, and so on. In further embodiments, the symmetry evaluation can include an evaluation of a symmetrical operation for the body part, such as outward rotation of an arm, an inward rotation of an arm, etc. In other embodiments, the evaluation of motion of the body part includes a fine granular motion evaluation. In other embodiments, evaluation of motion of the body part can include evaluation of angle, force, or torque. In other embodiments, the evaluation of motion of the body part includes microexpression analysis. In yet other embodiments, the evaluation of motion of the body part includes kinematic sequence analysis. And in still other embodiments the evaluation of motion of the body part includes body part motion phase identification, or various combinations of the immediately preceding embodiments.

The flow 900 includes displaying motion 970 of a body part. The displaying motion of a body part can be rendered on a display such as a display coupled to an electronic device including a smart phone, a personal digital assistant (PDA), a tablet, a laptop computer, a television, a projector, and so on. The display can show motion of the body part based on the information that was received by the receiving unit. In embodiments, the display can show an animation 972 of the body part based on the motion of the body part based on the changes in electrical characteristics by the first stretch sensor. The animation can be a generic illustration of a body part, a cartoon version of the body part, etc. In other embodiments, the body part can be displayed in a context 974 of an overall body of which the body part is a portion thereof. The context can be indicated using an outline, a color, a texture, and so on. In further embodiments, the display can show a graph of the motion of the body part 976 based on the changes in electrical characteristics by the first stretch sensor. The graph can include a line graph, a bar graph, a pie chart, points on a graph, and so on.

Embodiments can comprise evaluation of motion of the body part, wherein the evaluation of motion of the body part is based on information from the communication unit. One example of the use of this is for detecting/diagnosing scapular dyskinesia. Scapular dyskinesia can be defined as poor control of the movement pattern of the shoulder blade (scapula) at rest and/or during movement of the arm. Lack of a stable scapulae creates shoulder joint, upper back and neck vulnerability to injury. Individuals typically at risk include overhead throwing athletes, athletes involved in racket sports, swimmers, climbers, and those suffering from various neurologic disorders, such as stroke. However, quantifying scapulae dyskinesia is a challenge for clinicians. The scapula moves beneath the skin so markers on the skin only follow the scapulae for short distance. Also, the scapulae move in multiple planes. Currently, quantification consists of using a scale of severity based on observation of the scapula during arm elevation activities.

Movement pattern sequence analysis for scapular dyskinesia is enabled by using a stretch sensor diagonally across each scapula, forming a wide "V" shape on the upper back, in addition to a stretch sensor running horizontally from scapula tip-to-tip just below the base of the neck. Data from the communication units of each stretch sensor is analyzed to provide an evaluation of motion which provides a movement pattern sequence analysis. Therefore, in embodiments, the evaluation of motion of the body part includes scapulae movement pattern sequence analysis. In other embodiments, the scapulae movement pattern sequence analysis comprises an objective measurement of scapular dyskinesia. Various steps in the flow 900 may be changed in order, repeated, omitted, or the like without departing from the disclosed concepts. In embodiments, computer program product code can cause one or more processors to perform operations of displaying the motion of the body part.

Figure 10:
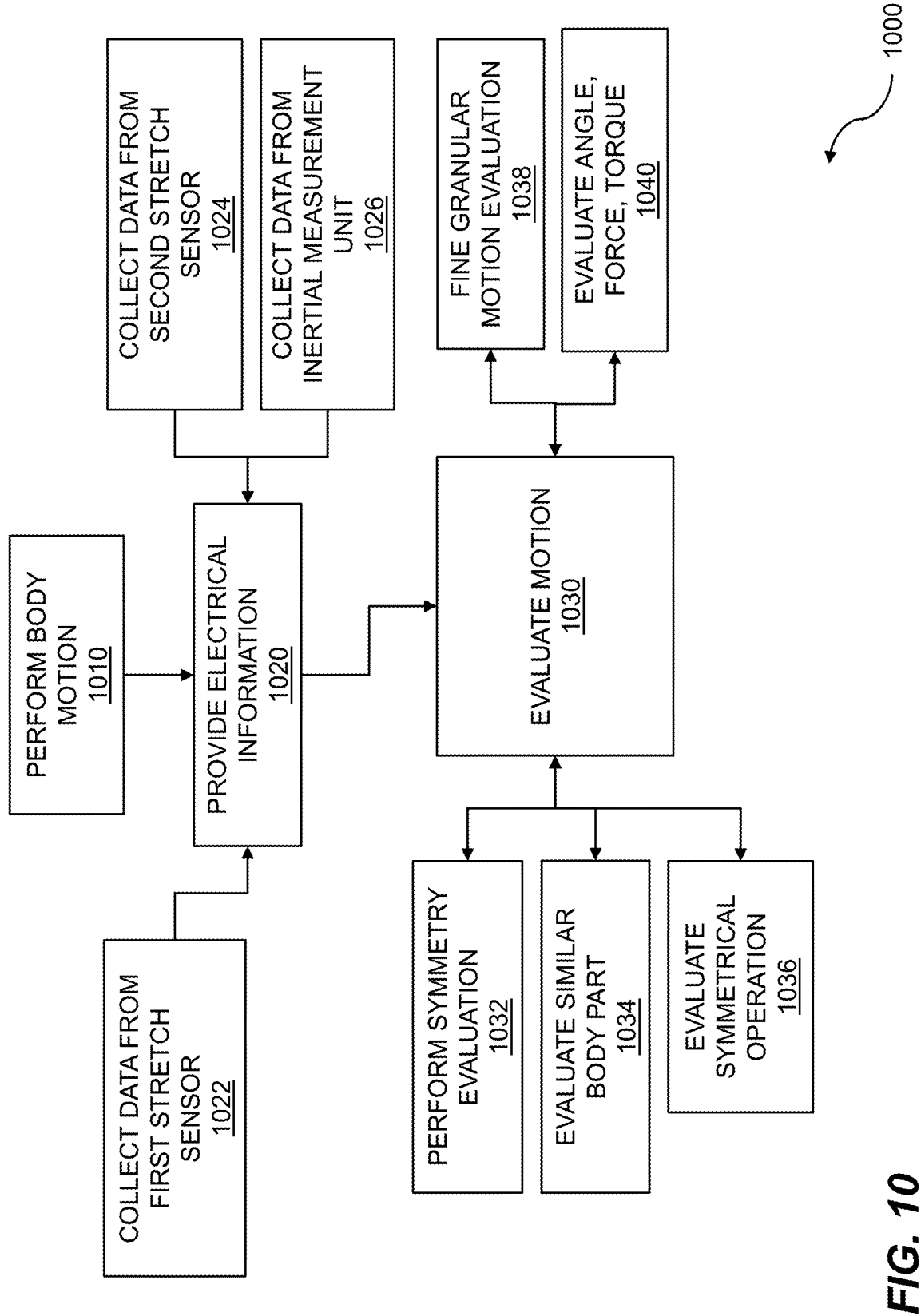
FIG. 10 is a flow diagram showing body motion and associated evaluation.

FIG. 10 is a flow diagram showing body motion and associated evaluation. Wearable sensors are used for body part motion analysis. The system includes a stretch sensor, where the stretch sensor changes electrical characteristics as the stretch sensor stretches. The stretch sensor is attachable via hooks to tape applied to a body part. A sensor collects changes in electrical characteristics by the stretch sensor as the body part moves. A communication unit provides information from the sensor to a receiving unit. The received information is display. The flow 1000 includes performing body motion 1010. As previously discussed, a stretch sensor is attachable to tape applied to a body part. As the body part moves, electrical characteristics of the stretch sensor change. The flow 1000 includes providing electrical information 1020, where the electrical information can include electrical change information. The electrical information can include resistance, capacitance, impedance, and/or inductance. Data can be collected from a first stretch sensor 1022. The first stretch sensor can include a strain gauge, an accelerometer, an electroactive polymer, and so on. Data can be collected from a second stretch sensor 1024. In embodiments, a second stretch sensor, can be used for measuring motion of the body part, where the second stretch sensor can stretch in a single dimension that can be substantially at a right angle to the first stretch sensor. Data can be collected from an inertial measurement unit (IMU) 1026. The IMU can measure specific force, angular rate, etc.

The flow 1000 includes evaluating motion 1030. The motion can be related to motion of a given body part. The motion of the body part can include linear displacement, angular displacement, location, and so on. The evaluation of motion can be performed to measure characteristics of the body part, to determine treatment for the body part, and so on. In embodiments, evaluation of motion of the body part can include performing a symmetry evaluation 1032. The symmetry evaluation can include an evaluation of a similar body part 1034 such as a left or right shoulder, elbow, wrist, hip, knee, ankle, and so on. In embodiments, the symmetry evaluation includes an evaluation of a symmetrical operation for the body part 1036, such as the amount of flex of the left knee compared to the right knee, the left shoulder compared to the right shoulder, etc. The evaluation of motion of the body part can include a fine granular motion evaluation 1038. The fine granular motion evaluation can be based on details relating to movement of the body part. The evaluation of motion of the body part can include evaluation of angle, force, or torque 1040. The evaluation of body part angle, force, or torque can be performed to determine the health of the body part, to determine treatment for the body part, to measure progress of treatment of the body part, and so on. Various steps in the flow 1000 may be changed in order, repeated, omitted, or the like without departing from the disclosed concepts.

Figure 11:
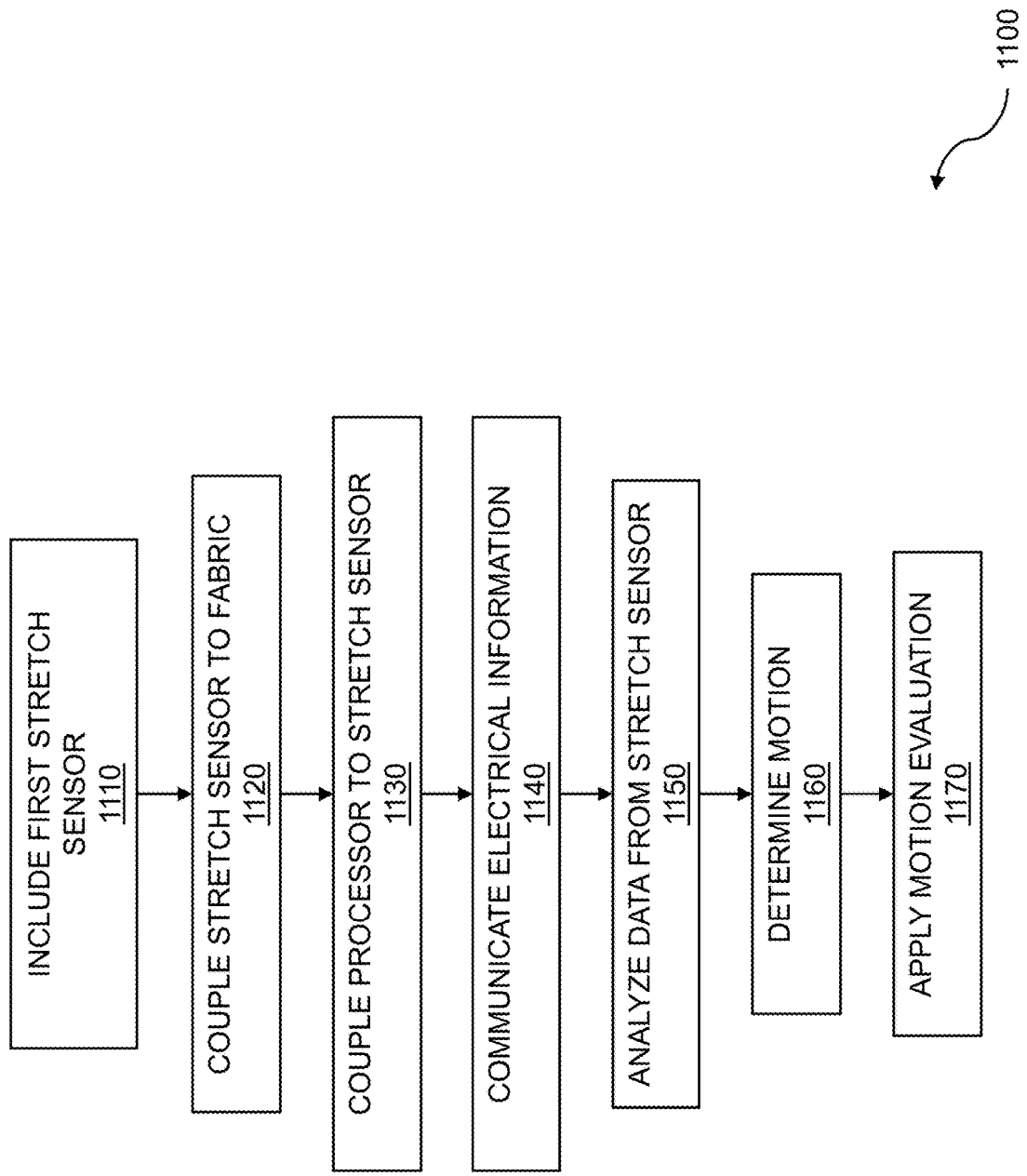
FIG. 11 is a flow diagram for sensor usage.

FIG. 11 is a flow diagram for sensor usage. Wearable sensors can be used for body part motion analysis. A first stretch sensor changes electrical characteristics as the sensor stretches. The first stretch sensor can be attachable to a body part using hooks that can couple the sensor to tape such as physical therapy tape, therapeutic kinesiology tape, and so on. A sensor collects the changes in electrical characteristics of the stretch sensor based on motion of the body part. A communication unit provides information from the sensor to a receiving unit. Received data is displayed as an animation of the body part, in a context of an overall body, and so on. The flow 1100 includes a first stretch sensor 1110. The first stretch sensor can be based on a variety of techniques including using electroactive polymers for the stretch sensor. Other techniques can include using strain gauges, using inertial measurement units (IMU), and so on. The flow 1100 includes coupling the body sensor to fabric 1120. The fabric can include a knitted fabric, a woven fabric, tape, and so on. In embodiments, tape can be attached to the body part where the first stretch sensor can be attached to the tape. Various types of tape can be attached to the body part. In embodiments, the tape includes physical therapy tape. In other embodiments, the tape includes therapeutic kinesiology tape.

The flow 1100 includes coupling a processor to the body sensor 1130. The processor can include a power source, a communication unit, an electrical characteristic calculation unit, and other components related to processing electrical change information from the stretch sensor. The processor can be used to drive the stretch sensor, to collect changes in electrical characteristics by the change sensor, etc. The flow 1100 includes communicating electrical information 1140. The communication of electrical information can include providing information from the sensor based on changes in electrical characteristics by the first stretch sensor. The communicating can include providing information using Bluetooth™, Wi-Fi, Zigbee™, infrared (IR), and other communication modes suitable for providing information. The electrical characteristics that can change based on stretching of the stretch sensor can include resistance, capacitance, impedance, and/or inductance. The flow 1100 includes analyzing data from the body sensor 1150. The analyzing can include analyzing the changes in electrical characteristics by the stretch sensor. The analyzing can include displacement including linear displacement, angular displacement, acceleration, location, magnetic field, etc. The flow 1100 includes determining deformation 1160. The deformation can include deformation of a stretch sensor, an inertial measurement unit (IMU) and so on. The deformation can include deformation of a body part, displacement of a body part, muscle bulge, and so on. The flow 1100 includes applying the motion evaluation 1170 to a downstream process such as medical diagnosis, sports injury rehabilitation, sports evaluation and training, to name just a few. Various steps in the flow 1100 may be changed in order, repeated, omitted, or the like without departing from the disclosed concepts.

Figure 12:
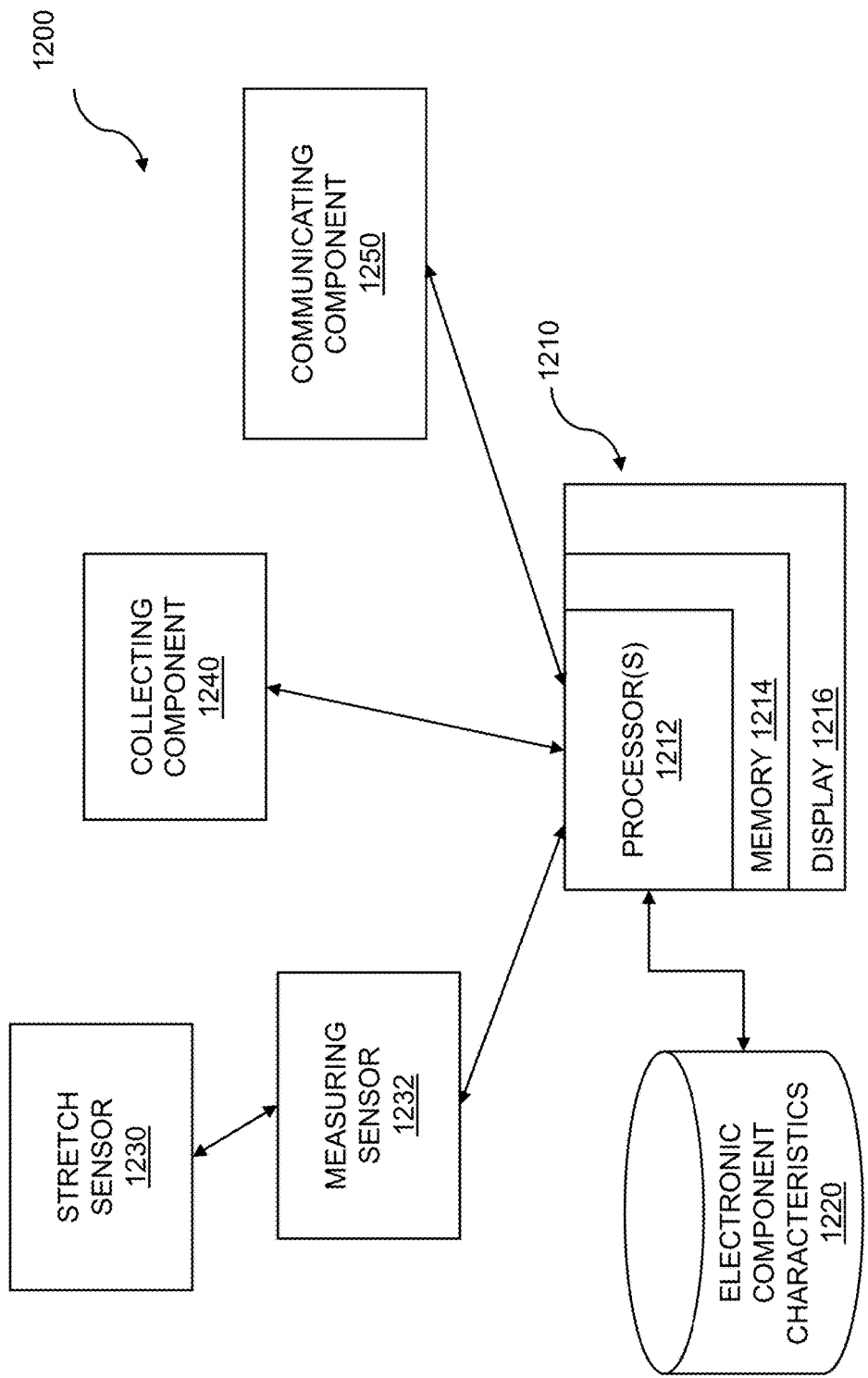
FIG. 12 is a system for body motion analysis.

FIG. 12 is a system for body motion analysis. Wearable sensors can be used to analyze body part motion. Tape can be applied to the body part and a stretch sensor can be attached to the tape using hooks. The stretch sensor can change electrical characteristics as it stretches. A sensor coupled to the stretch sensor can collect changes in electrical characteristics based on motion of the body part. The motion of the body part can include muscle bulge. A communication unit can provide information from the sensor to a receiving unit. Motion of the body part can be shown on a display. The displayed body part can be an animation and can be displayed in the context of an overall body. The data relating to the deformation of the body part can be used for body part treatment including medical techniques, physical therapy, occupational therapy, athletic training, strengthening, flexibility, endurance, conditioning, or rehabilitation therapy treatment.

The system 1200 can include a collecting component 1240, a communication component 1250, an electronic component characteristics module 1220, and an analysis computer 1210. The analysis computer 1210 can comprise one or more processors 1212, a memory 1214 coupled to the one or more processors 1212, and a display 1216 configured and disposed to present user interface information including graphical user interface information. The electronic component characteristics module 1220 can include a database and/or lookup table including empirically derived values, and can also include calibration data. The system 1200 can be supplied data from stretch sensor 1230 and measuring sensor 1232. The communicating component 1250 can comprise one or more communications devices, a battery coupled to the one or more communications devices, and so on. The collecting component 1240 can include resistance and/or capacitance measuring hardware and can include hardware for measuring current, voltage, resistance, capacitance, impedance, and/or inductance. A generating component (not shown) can include hardware for generating direct current and/or alternating current signals used for obtaining resistance and/or capacitance measurements. Typically, the current values are low (e.g. microamperes) and in embodiments, the frequency range includes signals from about 100 hertz to about 1 megahertz.

The system 1200 can include a computer program product embodied in a non-transitory computer readable medium for motion analysis, the computer program product comprising code which causes one or more processors to perform operations of: measuring body motion using a device comprising: a first stretch sensor wherein: the first stretch sensor varies electrical characteristics as the first stretch sensor stretches; and the first stretch sensor is attachable to a body part; a measuring sensor coupled to the first stretch sensor that collects changes in the electrical characteristics by the first stretch sensor based on motion of the body part; and a communication unit, coupled to the measuring sensor, that provides information from the measuring sensor on the changes in the electrical characteristics by the first stretch sensor; and displaying results of the measuring of the body motion.

Each of the above methods may be executed on one or more processors on one or more computer systems. Embodiments may include various forms of distributed computing, client/server computing, and cloud-based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above-mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the foregoing examples should not limit the spirit and scope of the present invention; rather it should be understood in the broadest sense allowable by law.

What is claimed is:

1. A system for motion analysis comprising:
 a first stretch sensor wherein:
  the first stretch sensor varies electrical characteristics as the first stretch sensor stretches; and
  the first stretch sensor is attachable to a body part;
 a measuring sensor coupled to the first stretch sensor that collects changes in the electrical characteristics by the first stretch sensor based on motion of the body part;
 a communication unit, coupled to the measuring sensor, that provides information from the measuring sensor on the changes in the electrical characteristics by the first stretch sensor; and
 an inertial measurement unit (IMU), coupled to the communication unit, that provides augmented information on motion of the body part, wherein the information from the measuring sensor and the augmented information from the IMU are analyzed to provide muscle activation and deformation characteristics, wherein the muscle activation comprises timing and displacement of muscle deformation.

2. The system of claim 1 further comprising a receiving unit, separate from the first stretch sensor, the measuring sensor, and the communication unit, that receives the information from the communication unit.

3. The system of claim 2 further comprising a display showing motion of the body part based on the information that was received by the receiving unit.

4. The system of claim 3 wherein the display shows an animation of the body part based on the motion of the body part based on the changes in the electrical characteristics by the first stretch sensor.

5. The system of claim 4 wherein the body part is displayed in a context of an overall body of which the body part is a portion thereof.

6. The system of claim 3 further comprising computer program product code which causes one or more processors to perform operations of displaying the motion of the body part.

7. The system of claim 1 wherein the first stretch sensor comprises an electroactive polymer.

8. The system of claim 1 wherein the first stretch sensor stretches in a single dimension.

9. The system of claim 8 further comprising a second stretch sensor, used for measuring motion of the body part, wherein the second stretch sensor stretches in a single dimension that is substantially different from the first stretch sensor.

10. The system of claim 1 wherein the first stretch sensor senses area variations for the first stretch sensor to produce the changes in the electrical characteristics.

11. The system of claim 1 wherein the first stretch sensor senses variations in a muscle bulge due to the changes in the electrical characteristics.

12. The system of claim 1 further comprising tape attached to the body part wherein the first stretch sensor is attached to the tape.

13. The system of claim 12 wherein the tape comprises physical therapy tape or therapeutic kinesiology tape.

14. The system of claim 1 further comprising evaluation of motion of the body part, wherein the evaluation of motion of the body part is based on information from the communication unit.

15. The system of claim 14 wherein the evaluation of motion of the body part includes performing a symmetry evaluation.

16. The system of claim 15 wherein the symmetry evaluation includes an evaluation of a symmetrical operation for the body part.

17. The system of claim 14 wherein the evaluation of motion of the body part includes microexpression analysis.

18. The system of claim 14 wherein the evaluation of motion of the body part includes kinematic sequence analysis.

19. The system of claim 14 wherein the evaluation of motion of the body part includes scapulae movement pattern sequence analysis.

20. The system of claim 19 wherein the scapulae movement pattern sequence analysis comprises an objective measurement of scapular dyskinesia.

21. The system of claim 1 further comprising a display showing motion of the body part, wherein the display shows an animation of the body part based on the changes in the electrical characteristics collected by the first stretch sensor.

22. The system of claim 1 wherein the first stretch sensor is attached to a targeted muscle group over a predetermined location of greatest muscle mass displacement.

23. The system of claim 1 wherein the muscle activation and deformation characteristics include a measured amount of time for reaching peak muscle contraction.

24. A processor-implemented method for motion analysis comprising:
    measuring body motion using a device comprising:
        a first stretch sensor wherein:
            the first stretch sensor varies electrical characteristics as the first stretch sensor stretches; and
            the first stretch sensor is attachable to a body part;
        a measuring sensor coupled to the first stretch sensor that collects changes in the electrical characteristics by the first stretch sensor based on motion of the body part;
        a communication unit, coupled to the measuring sensor, that provides information from the measuring sensor on the changes in the electrical characteristics by the first stretch sensor; and
        an inertial measurement unit (IMU), coupled to the communication unit, that provides augmented information on motion of the body part, wherein the information from the measuring sensor and the augmented information from the IMU are analyzed to provide muscle activation and deformation characteristics, wherein the muscle activation comprises timing and displacement of muscle deformation; and
    displaying results of the measuring of the body motion.

25. A computer program product embodied in a non-transitory computer readable medium for motion analysis, the computer program product comprising code which causes one or more processors to perform operations of:
    measuring body motion using a device comprising:
        a first stretch sensor wherein:
            the first stretch sensor varies electrical characteristics as the first stretch sensor stretches; and
            the first stretch sensor is attachable to a body part;
        a measuring sensor coupled to the first stretch sensor that collects changes in the electrical characteristics by the first stretch sensor based on motion of the body part;
        a communication unit, coupled to the measuring sensor, that provides information from the measuring sensor on the changes in the electrical characteristics by the first stretch sensor; and
        an inertial measurement unit (IMU), coupled to the communication unit, that provides augmented information on motion of the body part, wherein the information from the measuring sensor and the augmented information from the IMU are analyzed to provide muscle activation and deformation characteristics, wherein the muscle activation comprises timing and displacement of muscle deformation; and
    displaying results of the measuring of the body motion.

* * * * *